United States Patent [19]
Mosbach et al.

[11] Patent Number: 5,821,311
[45] Date of Patent: Oct. 13, 1998

[54] STABILIZERS, POLYMERS, AND EMULSIONS USEFUL FOR MOLECULAR IMPRINTING TECHNOLOGY

[76] Inventors: Klaus Mosbach, Hofwiesen Strasse No. 12, 8057, Zurich, Switzerland; Andrew G. Mayes, 22, St. Mary's St., Eynesbury, St. Neots, Cambridgeshire, PE19 2TA, England

[21] Appl. No.: 682,852

[22] Filed: Jul. 5, 1996

Related U.S. Application Data

[62] Division of Ser. No. 451,711, May 26, 1995, abandoned.

[51] Int. Cl.$^6$ .......................................................... C08F 2/00
[52] U.S. Cl. .......................... 526/201; 526/199; 526/200; 526/215; 526/243; 526/318.43; 526/326.2; 526/326.3
[58] Field of Search ...................... 526/201, 243, 526/215, 318.43, 199, 200, 326.2, 326.3

[56] References Cited

U.S. PATENT DOCUMENTS

| | | |
|---|---|---|
| 3,398,182 | 8/1968 | Guenthner et al. ............... 558/239 |
| 3,968,066 | 7/1976 | Mueller . |
| 4,035,506 | 7/1977 | Lucas et al. . |
| 4,144,367 | 3/1979 | Landucci . |
| 4,156,696 | 5/1979 | Koshar . |
| 4,356,273 | 10/1982 | Soch . |
| 4,414,355 | 11/1983 | Pokorny . |
| 4,415,694 | 11/1983 | Roiko et al. . |
| 4,455,348 | 6/1984 | Pokorny . |
| 4,487,876 | 12/1984 | Pokorny . |
| 4,504,401 | 3/1985 | Matsuo et al. . |
| 4,566,981 | 1/1986 | Howells . |
| 4,606,737 | 8/1986 | Stern . |
| 4,668,406 | 5/1987 | Chang . |
| 4,668,726 | 5/1987 | Howells . |
| 4,748,267 | 5/1988 | Chang . |
| 4,767,545 | 8/1988 | Karydas et al. . |
| 4,769,160 | 9/1988 | Karydas . |
| 4,788,287 | 11/1988 | Mastsuo et al. . |
| 4,835,300 | 5/1989 | Fukui et al. . |
| 4,840,675 | 6/1989 | Fukui et al. . |
| 4,921,696 | 5/1990 | Vander Meer et al. . |
| 5,010,153 | 4/1991 | Famili et al. ............... 526/243 |
| 5,055,538 | 10/1991 | Amimoto et al. ............... 526/245 |
| 5,061,766 | 10/1991 | Yamashita et al. ............... 526/191 |
| 5,093,398 | 3/1992 | Röttger et al. ............... 526/322 |
| 5,093,445 | 3/1992 | Podszun et al. ............... 526/243 |
| 5,098,774 | 3/1992 | Chang . |
| 5,100,954 | 3/1992 | Itoh et al. . |
| 5,126,379 | 6/1992 | Volkert et al. . |
| 5,133,802 | 7/1992 | Maekawa et al. . |
| 5,159,105 | 10/1992 | Hansen et al. . |
| 5,202,359 | 4/1993 | McIntyre . |
| 5,216,097 | 6/1993 | Allewaert et al. . |
| 5,258,458 | 11/1993 | Allewaert et al. . |
| 5,286,352 | 2/1994 | Hansen et al. . |
| 5,344,956 | 9/1994 | Allewaert et al. . |
| 5,516,337 | 5/1996 | Nguyen . |
| 5,580,645 | 12/1996 | Kirchner . |
| 5,587,413 | 12/1996 | Enokida et al. . |

FOREIGN PATENT DOCUMENTS

| | | |
|---|---|---|
| 0 364 772 | 9/1989 | European Pat. Off. . |
| WO 92/19663 | 11/1992 | European Pat. Off. . |
| 0 552 630 | 1/1993 | European Pat. Off. . |
| 64-14221 | 7/1987 | Japan . |

OTHER PUBLICATIONS

Klaus Mosbach; *Scientific America*; "Enzymes Bound to Artificial Matrixes"; pp. 26–33; Mar. 1971.

Ann–Christin Johansson and Klaus Mosbach; *Biochimica et Biophysica Acta* "Acrylic Copolymers As Matrices for the Immobilization of Enzymes"; pp. 339–347; Jun. 10, 1974.

H. Nilsson, R. Mosbach, and K. Mosbach; *Biochimica et Biophysica Acta*; "The Use of Bead Polymerization of Acrylin Monomers for Immobilization of Enzymes"; pp. 253–256; Feb. 18, 1972.

*Primary Examiner*—Joseph L. Schofer
*Assistant Examiner*—N. Sarofim
*Attorney, Agent, or Firm*—Morgan & Finnegan, L.L.P.

[57] ABSTRACT

The claimed invention is directed to stabilizers, polymers, and emulsifiers useful in preparing molecularly imprinted materials having recognition capabilities corresponding to the imprint molecule.

10 Claims, 5 Drawing Sheets

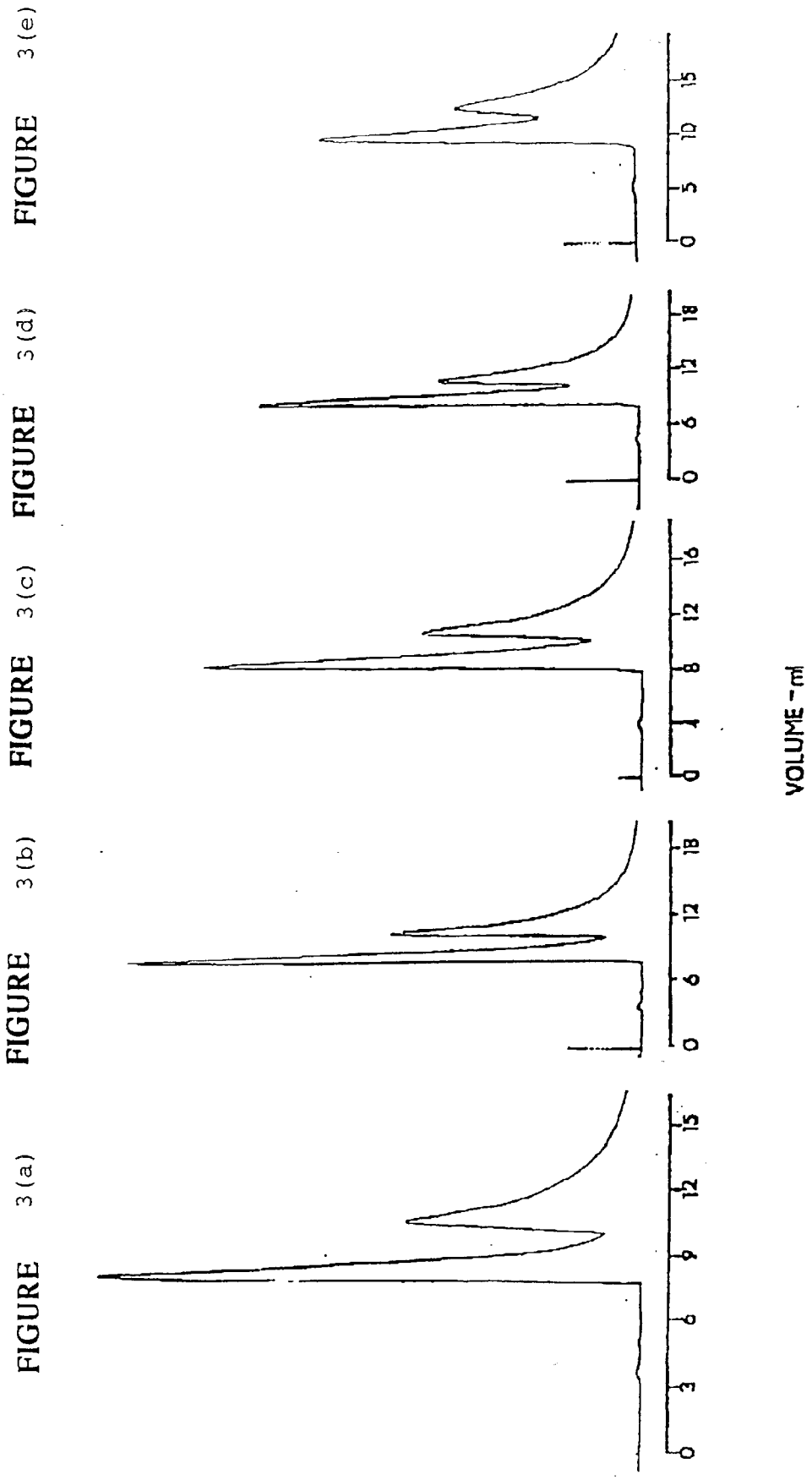

STABILIZERS, POLYMERS, AND EMULSIONS USEFUL FOR MOLECULAR IMPRINTING TECHNOLOGY

CROSS-REFERENCE TO RELATED APPLICATIONS

This application is a divisional of U.S. Ser. No. 08/451,711 filed May 26, 1995 now abandoned. The entire contents of this prior application are incorporated herein by reference.

FIELD OF THE INVENTION

The present invention relates to molecularly imprinted polymer supports and a method of making these supports. More specifically the present invention involves arranging polymerizable functional monomers around a print molecule using suspension polymerization techniques which is accomplished with a stabilizing copolymer having the following formula:

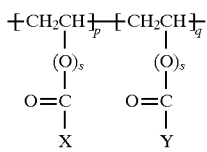

wherein:

X is $C_nF_{2n+1}$, $C_nF_{2n+1}(CH_2)_rO$—, $C_nF_{2n+1}O$— or $C_nF_{2n+1}SO_2N(C_2H_5)C_2H_4$—O;

Y is $(Z)_tCH_3O(CH_2CH_2O)_mC_2H_4$—O or $(Z)_tCH_3O(CH_2CH_2O)_m$;

Z is a print molecule;

n is between 1 and 20;

m can be zero to about 500;

p is at least 1;

q can be zero or any positive number;

r is 1–20, preferably 1 or 2;

s is zero or 1; and t is zero or 1.

The polymer support of the present invention is preferably in bead form and is capable of separating or resolving amino acids, amino-acid derivatives, pharmaceutical compounds and poly-saccharides.

BACKGROUND OF THE INVENTION

Molecular imprinting, also referred to as templating, has been used for chiral separations and involves arranging polymerizable functional monomers around a print molecule. This is achieved either by utilizing non-covalent interactions such as hydrogen bonds, ion-pair interactions, etc. (non-covalent imprinting), or by reversible covalent inter-actions (covalent imprinting) between the print molecule and the functional monomers. The resulting complexes are then incorporated by polymerization into a highly cross-linked macroporous polymer matrix. Extraction of the print molecule leaves sites in the polymer with specific shape and functional groups complementary to the original print molecule. Mosbach, K., *Trends in Biochemical Sciences*, Vol. 7, pp. 92–96, 1994; Wulff, G., *Trends in Biotechnology*, Vol. 11, pp. 85–87, 1993; and Andersson, et al., *Molecular Interactions in Bioseparations* (Ngo. T. T. ed.), pp. 383–394.

Different racemic compounds have been resolved via molecular imprinting, i.e., "amino acid derivatives", see Andersson, et al., *Molecular Interactions in Bioseparations* (Ngo T. T. ed.), Plenum Press, pp. 383–394, 1993; "drugs", Fischer, et al., *J. Am. Chem. Soc.*, 113, pp. 9358–9360, 1991; Kempe, et al., *J. Chromatogr.*, Vol. 664, pp. 276–279, 1994; and "sugars", Wulff, et al., *J. Org. Chem.*, Vol. 56, pp. 395–400, 1991; Mayes, et al., *Anal. Biochem.*, Vol. 222, pp. 483–488, 1994. Baseline resolution has been achieved in many cases.

An advantage of molecularly imprinted polymers, in contrast to other chiral stationary phases, is the predictable order of elution of enantiomers. Imprintable supports have been prepared from bulk polymerization techniques, using a porogenic solvent to create a block of macroporous polymer. However, bulk polymerization supports must be crushed, ground and sieved to produce appropriate particle sizes for use in separatory columns and analytical protocols. For example, in chromatographic evaluations, polymer particles smaller than 25 μm are generally used. However, from the bulk polymerization process the grinding process used to provide these smaller particles from the bulk polymerization process is unsatisfactory. Grinding produces irregularly shaped particles and an excessive and undesirable quantities of "fines." Typically less than 50 percent (50%) of the ground polymer is recovered as useable particles. Irregular particles generally give less efficient column packing for chromatography and often prove troublesome in process scale-up. Hence, uniformly shaped particles, e.g. beaded polymers, would be preferable in most cases. The grinding process also requires an additional treating step to remove the fines, i.e., sedimentation. This is costly and time consuming. The bulk polymerization and necessary grinding process makes this prior art technique labor intensive, wasteful and unacceptable.

Attempts have been made to use suspension and dispersion polymerization techniques for producing beads from acrylic monomers which can contain imprinted molecules. In principle these suspension and dispersion polymerization techniques should offer an alternative to bulk polymerization. However, existing suspension and dispersion techniques are not satisfactory because water or a highly polar organic solvent (e.g. an alcohol) is used as the continuous phase for the relatively hydrophobic monomers. These solvents are incompatible with most covalent and non-covalent imprinting mixtures due to the competition between solvent and functional monomers for specific interaction with the print molecule. Since suspension polymerization techniques use the solvent in large molar excess, the solvents saturate the monomer phase and drastically reduce the number and strength of the inter-actions between functional monomers and print molecules. In addition, because of the high solubility of acidic monomers in water, random copolymerization of monomers and cross-linker is probably not achieved. Water soluble print molecules are also lost due to partitioning into the aqueous phase. Not unexpectedly, attempts to make molecularly imprinted polymer beads by suspension polymerization in water have led to only very poor recognition. Damen, et al., *J. Am. Chem. Soc.*, Vol. 102, pp. 3265–3267, 1980; Braun, et al., *Chemiker-Zeitung*, Vol. 108, pp. 255–257, 1984; Byström, et al., *J. Am. Chem. Soc.*, Vol. 115, pp. 2081–2083, 1993. With stable covalent or metal chelate bonds between functional monomers and print molecules prior to polymerization, it may be possible to use aqueous conditions.

Attempts have also been made to produce composite beaded particles by imprinting in the pore network of performed beaded silica, Norrlow, et al., *J. Chromatogr.*, Vol. 299, pp. 29–41, 1924; Wulff, et al., *Reactive Polymers*, Vol. 3, pp. 261–2757, 1985 or TRIM. However, the preparation requires careful handling and the volume of imprinted polymer per unit column is inevitably reduced by the beads themselves.

Sellergren, B., J. Chromatogr., Vol. 673, pp. 133–141, 1994 and Sellergren, B., Anal. Chem., Vol. 66, pp. 1578–1582, 1994, report the use of dispersion polymerization in a polar solvent mixture for molecular imprinting. The process produces random precipitates rather than regular beads. Acceptable results were only achieved for highly charged print molecules, presumably due to the presence of competing solvent effects.

Thus, a need exists for a method that produces beaded polymers containing molecular imprints that is simple and reproducible, does not compromise the quality of the imprints obtained and eliminates the need for grinding and sieving equipment. A need also exists for a molecular imprinted polymer bead that is uniform.

SUMMARY OF THE INVENTION

The present invention relates to molecular imprinted polymer supports and their preparation via suspension polymerization. The suspension techniques according to the present invention provide for molecular imprinting by using a perfluorocarbon liquid containing polyoxyethylene ester groups as the dispersing phase. The perfluoro-carbon-polyoxyethylene ester containing group compound does not interfere with the interactions between functional monomers and print molecules that are required for the recognition process during molecular imprinting. Controllable "support" particle sizes from about 2 $\mu$m to about 100 $\mu$m are obtained by varying the amount of stabilizing polymer, or agitating technique.

Accordingly, it is an object of the present invention to provide a method that enables imprinted polymers to be easily produced, in beaded form with an almost quantitative yield of useable material.

It is another object of the present invention to provide a fluorocarbon copolymer that stabilizes the emulsion in suspension polymerization processing without interfering with the interactions between functional monomers and print molecules.

It is a still further object to stabilize an emulsion of functional monomers, cross-linkers, print molecules, initiators and porogenic solvents.

Another object of the present invention is to provide molecularly imprinted polymer bead having a size of about 2 to about 100 $\mu$m, in high yield.

A still further object of the present invention is to provide small, about 2–5 $\mu$m, beaded packings that provide low back pressure, rapid diffusion, and good separation at high flow rates.

These and other objects and advantages will become more apparent in view of the following description and attached drawings.

BRIEF DESCRIPTION OF THE DRAWINGS

FIGS. 3a–3e show HPLC traces showing separation of Boc-D,L-Phe by a 25 cm column of Example PF15 (5 $\mu$m TRIM beads). Conditions: the column was equilibrated with chloroform+0.25% acetic acid; 1 mg Boc-D,L-Phe in 20 $\mu$l mobile phase was injected and eluted with the same solvent at flow rates of 3(a) 0.5 mlmin$^{-1}$; 3(b) 1 mlmin$^{-1}$; 3(c) 2 mlmin$^{-1}$; 3(d) 3 mlmin$^{-1}$; and 3(e) 5 ml-min$^{-1}$. At 0.5 ml-min$^{-1}$, f/g=0.89, Rs=1.36 and $\alpha$=1.52 f/g values were 0.89, 0.89, 0.85, 0.76 and 0.61 at 0.5, 1, 2, 3 and 5 mlmin$^{-1}$ respectively.

DETAILED DESCRIPTION OF THE INVENTION

Figure 1:
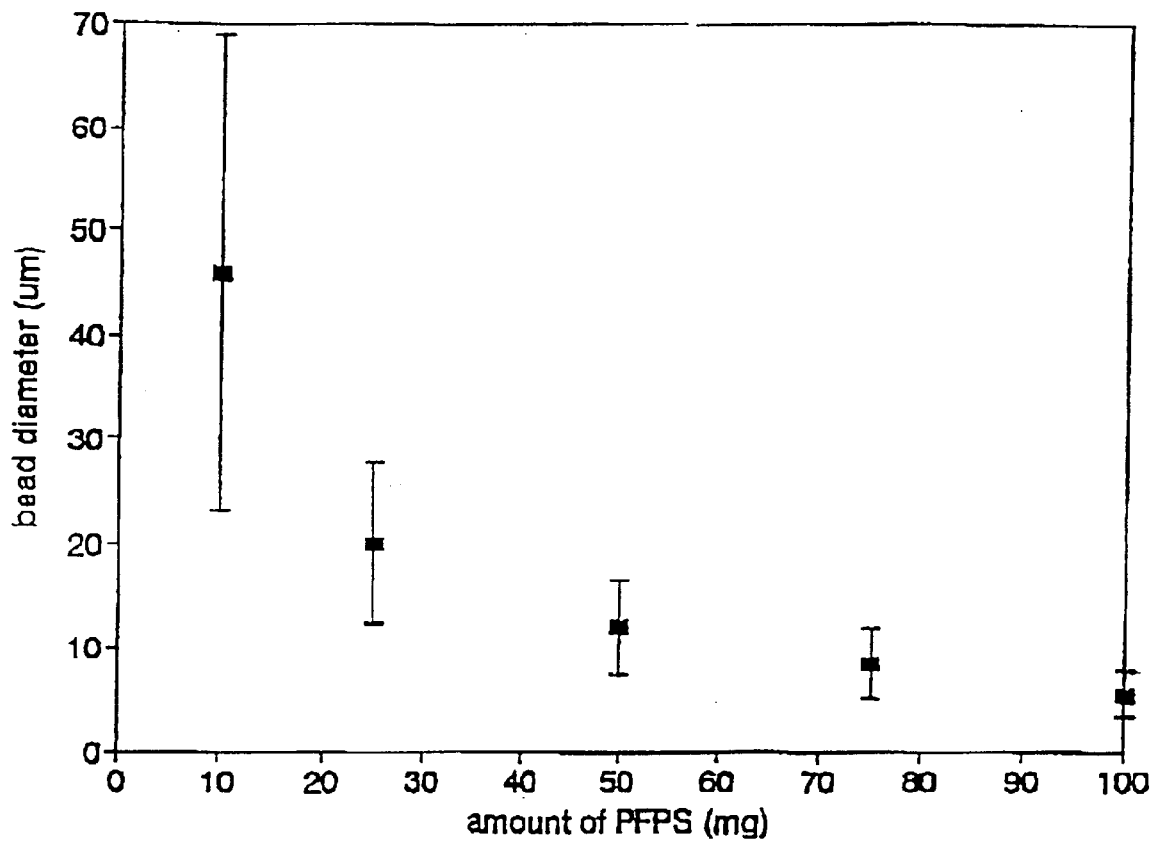
FIG. 1 shows a graph of bead diameter versus PFPS quantity added for a "standard polymerization" containing 1.84 g EDMA, 0.16 g MAA, 4.2 g chloroform and 20 mg AIBN emulsified in 20 ml PMC.

According to the present invention, a suspension polymerization technique based on emulsion of noncovalent imprinting mixtures formed in liquid perfluorocarbons that contain polyoxyethylene ester groups, is provided. Most prior art suspension and dispersion techniques use water or a highly polar organic solvent (e.g. an alcohol) as the continuous phase for the relatively hydrophobic monomers, which is not fully satisfactory. Accordingly, a different approach is required. The present invention provides the "different approach." In addition, the drawbacks of prior art processes, e.g., solvents that are incompatible with most covalent and non-covalent imprinting mixtures due to the competition between solvent and functional monomers for specific interaction with the print molecule are avoided. The present invention avoids the use of dispersants which interfere with the interactions that are required for recognition between print molecules and functional monomers. In order to create reasonably stable emulsion droplets containing monomers, cross-linkers, print molecules, porogenic solvents, and fluorinated surfactants, the invention uses a perfluorocarbon polymer that also contains polyoxyethylene ester groups, with or without a print molecule for providing surface imprinting.

The stabilizing/dispersing agent of the present invention is generally defined by the following formula:

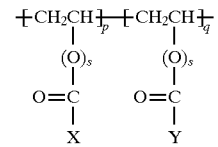

wherein:

X is $C_nF_{2n+1}$, $C_nF_{2n+1}(CH_2)_rO—$, $C_nF_{2n+1}O—$ or $C_nF_{2n+1}SO_2N(C_2H_5)C_2H_4—O$,

Y is $(Z)_tCH_3O(CH_2CH_2O)_mC_2H_4—O$ or $(Z)_tCH_3O(CH_2CH_2O)_m$;

Z is a print molecule;

n is between 1 and 20;

m can be zero to about 500;

p is at least 1;

q can be zero or any positive number;

r is 1–20, preferably 1 or 2;

s is zero or 1; and t is zero or 1.

Block, triblock and multiblock copolymers formed from the acrylated monomers of $C_nF_{2n+1}SO_2N(C_2H_5)C_2H_4—OH$ and $(Z)_tCH_3O(CH_2CH_2O)_mC_2H_4$—OH are also within the scope of the present invention. A preferred stabilizing/dispersing agent according to the present invention is a copolymer containing monomer A defined by the formula: $C_nF_{2n+1}SO_2N(C_2H_5)C_2H_4O$—CO—CH=$CH_2$; and comonomer B defined by the formula: $CH_3O(CH_2CH_2O)_mC_2H_4O$—CO—CH=$CH_2$; where n is between 1 and 20 and m is between 0 and 500. Preferably, n is about 7.5 and m is about 43. Most preferably, the stabilizing/dispersing agent is defined by the following formula,

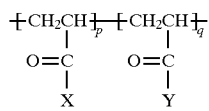

wherein:

X is $C_nF_{2n+1}SO_2N(C_2H_5)C_2H_4$—O;

Y is $(Z)_tCH_3O(CH_2CH_2O)_mC_2H_4$—O;

Z is a print molecule;

n is between 1 and 20;

m can be zero to about 500;

p is at least 1;

q can be zero or any positive number;

s is zero or 1;

t is zero or 1, and enables the production of spherical beads in high yields via a suspension polymerization process.

Preferably, m=about 7.5, n=about 43, p=about 19 and q=about 1. The values m, n, p, and q need not be whole numbers.

As a result of using the stabilizer of the present invention, the physical characterization of beads is achieved either by utilizing non-covalent interactions such as hydrogen bonds, ion-pair interactions, etc. (non-covalent imprinting), or by reversible covalent inter-actions (covalent imprinting) between the print molecule and the functional monomers. The complexes formed are then incorporated by polymerization into a highly cross-linked macroporous polymer matrix formed from the copolymerization of different acrylic monomers. Extraction of the print molecule leaves sites in the polymer with specific shape and functional groups complementary to the original print molecule.

The print molecules that can be used in the present invention include, but are not limited to:

1. D- and L-Boc tryptophans
2. D- and L-Boc phenylanalines
3. D- and L-phenylanalines
4. D- and L-Boc-proline-N-hydroxysuccinimide esters
5. D- and L-Cbz tryptophans
6. D- and L-Cbz-aspartic acids
7. D- and L-Cbz-glutamic acids
8. D- and L-Cbz-tryptophan methyl esters
9. nitrophenyl α and β, D-, L-galactosides
10. (S)-(–) timolol
11. D-fructose
12. D-galactose
13. phenyl α-D-mannopyranoside
14. acryl α and β glucosides
15. (R)-phenylsuccinic acid
16. Ac-L-Trp-OEz
17. L-PheβNA
18. L-LeuAn
19. L-PheAn
20. L-PheGlyAn
21. L-MenPheAn
22. L-PyMePheAn
23. L-PLPheAn
24. N-Ac-L-Phe-L-Trp-OMe
25. diazepham
26. propranolol
27. ephidrine However the Boc- D- and L-Phe, and L-Phe have been used in the following non-limiting examples.

REAGENT PREPARATION

Monomers

Ethylene glycol dimethacrylate (EDMA) and methacrylic acid (MAA) (Merck, Darmstadt, Germany) were distilled under reduced pressure prior to use. Trimethylolpropane trimethacrylate (TRIM) (Aldrich Chemie, Steinheim, Germany), styrene (Aldrich), methyl methacrylate (MMA) (Aldrich) and benzyl methacrylate BMA) (Polysciences, Warrington, Mass.) were used as received. 2,2'-azobis (2-methylpropionitrile (AIBN) came from Janssen Chimica, Goel, Belgium.

2-(N-ethylperfluoroalkylsulphonamido)ethanol (PFA-1) (Fluorochem, Old Glossop, UK), PEG2000 monomethyl-ether (MME) (Fluka Chemic A.G., Buchs, Switzerland) and PEG350MME (Sigma, St. Louis, Mo.) were converted to their acrylates by reaction with acryloyl chloride and triethylamine in dichloromethane, were also available commercially (from Fluorochem and Polysciences respectively). Perfluoro(methylcyclohexane) (PMC) and Fluorad FC430 were also obtained from Fluorochem.

Imprint Molecules

Boc-D-Phe, BocU-Phe and Boc-D, L-Phe were obtained from Bachem A.G., Bubendorf, Switzerland). (Boc(tert-butoxy carbonyl; Phe=phenylanaline).

Porogenic Solvents

Chloroform ($CHCl_3$) (HPLC grade) was passed down a basic alumina column to remove ethanol and stored over molecular sieves for use as porogenic solvent during imprinting. For HPLC it was used as received. Toluene was dried with sodium and acetonic with molecular sieves prior to use. Other solvents were of analytical grade or better and were used as received.

PREPARATION OF STABILIZERS

The most emulsion stabilizing/dispersing polymers (PFPS) according to the present invention are defined by the formula

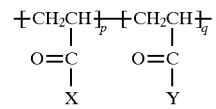

wherein:

X is $C_nF_{2n+1}SO_2N(C_2H_5)C_2H_4$—O;

Y is $(Z)_tCH_3O(CH_2CH_2O)_mC_2H_4$—O;

Z is a print molecule;

n is between 1 and 20;

m can be zero to about 500;

p is at least 1;

q can be zero or any positive number; and t is zero or 1; and in particular where n is about 7.5, m is about 43, p is about 19 and q is about 1.

EXAMPLE 1

4 g acryloyl PFA-1 (7.2 mmole) $C_nF_{2n+1}SO_2N(C_2H_5)$ $C_2H_4$—O—CO—CH=$CH_2$ and 0.76 g acryloyl PEG2000MME (0.36 mmole) defined by the following formula: $CH_3O(CH_2CH_2O)_mC_2H_4$—O—CO—CH=$CH_2$, were dissolved in 10 ml of chloroform, where n is about 7.5 and m is about 43.24 mg (76 μmole) of AIBN was added and dissolved oxygen removed by nitrogen sparring for 5 minutes. The tube was then sealed and the contents polymerized at 60° C. for 48 hours in a shaking water bath. The resulting solution was slightly turbid and became much more turbid on cooling. Most of the solvent was removed by slow evaporation at 30° C. under reduced pressure (to avoid foaming) and the remainder under reduced pressure at 60° C. The resulting polymer was a sticky pale yellow paste which was used without further treatment.

Other polymer stabilizers were synthesized in a similar fashion using the appropriate ratio of monomers and 1 mole % of AIBN. All formed cream to amber polymers varying from glassy to very soft pastes depending on the composition.

Suspension Polymerizations

The amount of porogenic solvent required to just saturate 20 ml PMC was determined. The required amount of PFPS was dissolved in this volume of porogenic solvent in a 50 ml borosilicate glass tube and 20 ml PMC added and shaken to give a uniform white to opalescent emulsion. 5 ml of "imprinting mixture", (Table 1) was added and emulsified by stirring at 2000 rpm for 5 minutes.

TABLE 1

| Ex.* | Print Molecule (mg) | MAA (g) | EDMA (g) | Solvent (g) | PFPS (mg) |
|---|---|---|---|---|---|
| PF1 | Boc—L—Phe (120) | 0.16 | 1.84 | $CHCl_3$ (4.2) | 10 |
| PF2 | Boc—L—Phe (120) | 0.16 | 1.84 | $CHCl_3$ (4.2) | 25 |
| PF3 | Boc—L—Phe (120) | 0.16 | 1.84 | $CHCl_3$ (4.2) | 50 |
| PF4 | Boc—L—Phe (120) | 0.16 | 1.84 | $CHCl_3$ (4.2) | 75 |
| PF5 | Boc—L—Phe (120) | 0.16 | 1.84 | $CHCl_3$ (4.2) | 100 |
| PF6 | Boc—L—Phe (120) | 0.16 | 1.84 | $CHCl_3$ (4.2) | 200 |
| PF7 | Boc—L—Phe (120) | 0.16 | 1.84 | $CHCl_3$ (4.2) | 500 |
| PF8 | Boc—L—Phe (120) | 0.32 | 1.84 | $CHCl_3$ (4.2) | 25 |
| PF9 | Boc—L—Phe (120) | 0.48 | 1.84 | $CHCl_3$ (4.2) | 25 |
| PF10 | Boc—L—Phe (120) | 0.64 | 1.84 | $CHCl_3$ (4.2) | 25 |
| PF11 | Boc—L—Phe (68) | 0.265 | 1.84 | $CHCl_3$ (4.2) | 25 |
| PF12 | Boc—D,L—Phe (120) | 0.16 | 1.84 | $CHCl_3$ (4.2) | 25 |
| PF13 | None | 0.16 | 1.84 | toluene (2.45) | 25 |
| PF14 | None | 0.16 | 1.84 | acetone (2.25) | 25 |
| PF15 | Boc—L—Phe (308) | 0.4 | 1.57 TRIM | $CHCl_3$ (4.6) | 100 |
| PF16 | Boc—L—Phe (308) | 0.4 | 1.57 TRIM | $CHCl_3$ (4.6) | 25 |

*The beads prepared according to the present invention, as well as the comparative examples, are designed with the PF code numbers in column 1 of the table.

The polymerization apparatus used for all polymerizations in the present invention comprised a 50 ml borosilicate glass tube with screw lid, the center of which was drilled to allow the shaft of a stainless steel flat blade stirrer to pass there through. The stirrer blade was about one-half the length of the tube. A rubber seal was used to reduce evaporation through this hole. An additional small hole in the lid allowed a nitrogen stream to be fed into the tube via a syringe needle. The tube was held vertically in a retort stand and stirred with an overhead stirrer. A UV lamp was placed about 5 cm away from the tube and the lamp and tube surrounded with aluminum foil to maximize reflected light.

Emulsions designated PF1–PF16 in Table 1 above were prepared and placed in the reactor which was purged with nitrogen for 5 minutes and then the emulsions polymerized by UV irradiation at 366 nm at room temperature under a gentle nitrogen stream stirring at 500 rpm. Polymerization was continued for 3 hours. The resulting polymer particles (beads) were filtered on a sintered glass funnel and the PMC recovered. The beads were washed extensively with acetone, sonicating to break up loose aggregates of beads (large aggregates were broken up by gentle crushing with a spatula), before drying and storing.

Varying the amount of PFPS used during the polymerization controls bead size, the relationship being shown in FIG. 1. FIG. 1 is a graph of the mean and standard deviation for beads made in accordance with the present invention using different amounts of PFPS. A standard was prepared with 2 g of monomers in a 5 ml total volume (see Table 1). 10 mg PFPS is at the lower limit of the range where stable emulsions can be formed and quite a lot of aggregate was also present in this sample. Using 150 mg or more of PFPS gave only very small irregular particles of 1–4 μm. No beads were apparent in these samples.

COMPARATIVE EXAMPLES

Two commercial fluorinated surfactants (polyfluoroalcohol (PFA-1) and fluorad FC430), a homopolymer of acryloyl PFA-1, a range of random copolymers of acryloyl PFA-1 with styrene, methyl methacrylate or benzyl methacrylate, and graft copolymers containing perfluoroester groups and PEG groups attached to the main acrylate chain, were also evaluated as stabilizers. Most of these, however, proved to be ineffective. The process was hindered by the high density of the dispersant which caused rapid "creaming" of the emulsion, thus favoring coalescence of dispersed droplets.

Polyacryloyl PFA-1, alone, was evaluated and gave sufficiently stable emulsions for suspension polymerization and gave good quality beads. Unfortunately, due to its poor solubility, this surfactant proved to be extremely difficult to remove from the surface of the beads after polymerization, resulting in extremely hydrophobic surfaces.

The most effective emulsion was achieved using a copolymer of acryloyl-PFA-1 and acryloyl-PEG2000MME (mole ratio 20:1-termed PFPS).

MOLECULARLY IMPRINTED BEAD PROPERTIES

Size

The type of emulsification impacts the polymerization process and the resulting molecularly imprinted beads. The preferred method involved stirring at about 2000 rpms for about 5 minutes and gave good uniformity and reproducibility for a bead having a size of between 2 and 25 μm. Five separate polymerizations performed on different days using 25 mg PFPS as the emulsifier gave a mean bead size of 19.7 μm and a standard error of 0.6 μm.

Emulsification in an ultrasonic bath for 5 minutes gave a much broader size distribution with an excessive quantity of small particles. Conventional shaking in a tube 3 or 4 times gave good results if larger beads were desired, i.e., 40 μm to about 100 μm.

The polymerization temperatures also affected the polymerization process and resulting beads. Attempts to use thermal initiation at 45° C. using ABDV as initiator gave only small irregular fragments. UV initiation of polymerization at 4° C. led to a large amount of aggregation. Most polymerizations were performed at ambient temperature (about 20° C.), i.e. at least about 18° C., although some temperature increase occurred during polymerization due to the proximity of the UV lamp. Polymerizations carried out during very warm weather, when ambient temperature reached 30° C., gave slightly smaller beads, indicating that polymerization temperature can also impact bead size while still providing reproducible results.

Polymerizations were also carried out in a range of solvents commonly used in molecular imprinting, e.g., chloroform, toluene, acetonitrile and acetone. The polymerization method can use all of these solvents and hence should be appropriate for most imprinting situations. However, the preferred solvents are chloroform, toluene and acetone. The size and race structure of the beads produced also depends on the porogenic solvent used. Both toluene (26 μm±12 μm–means±SD) and acetone (52 μm±15 μm) gave larger beads than chloroform (18 pm±8 pm) for 25 mg of PFPS in a "standard" polymerization.

Dead Size Distributions

Suspensions of beads in acetone were dried onto microscope slides and about 150 beads measured at random using a calibrated graticule in an optical microscope. Either 100× or 400× magnifications was used depending on the particle size. Some samples were also imaged by SEM. Measurements made from these images compared well with the results from optical determinations.

Scanning Electron Micrographs

Polymer beads were placed on aluminum pegs and sputter coated with 15 nm gold using a Polaron E5150 gold coater. Images were then obtained using an ISI 100A SEM at 25 kV in order to compare the sizes, surfaces and pore structures of beads produced under different conditions.

Scanning electron micrographs of some of the beaded polymer preparations are shown in FIGS. 2a–2e. The method according to the present invention produces substantially spherical beads, both for EDMA(2a–2d) and TRIM(2e) based polymers, and using a variety of porogenic solvents. The incidence of defects, such as surface indentations or small holes, is somewhat higher than is usually observed for water-based suspension polymerizations in water. The morphology of the beads is typical of beads made by suspension polymerization with a slightly denser and smoother surface layer covering a more porous structure in the interior.

Figures 2A, 2B:
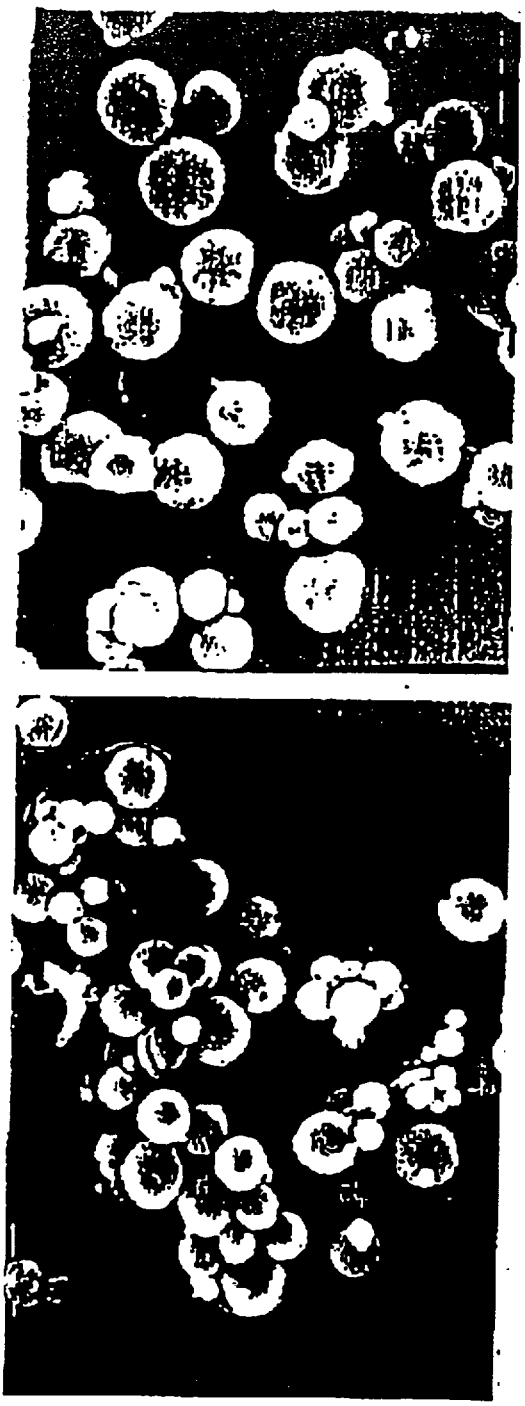
FIGS. 2a–2e show scanning electronmicrographs of beads produced from suspension polymerization in PMC in accordance with the present invention where the beads were placed on aluminum pegs and sputter coated with 15 mm gold using a polaron E5150 coater. The images were obtained using an ISI 100A SEM at 25 kV. The magnification is 500×. 2(a) PF2; 2(b) PF13; 2(c) PF13; 2(d) PF14; and 2(e) PF15.
Figures 2C, 2D:
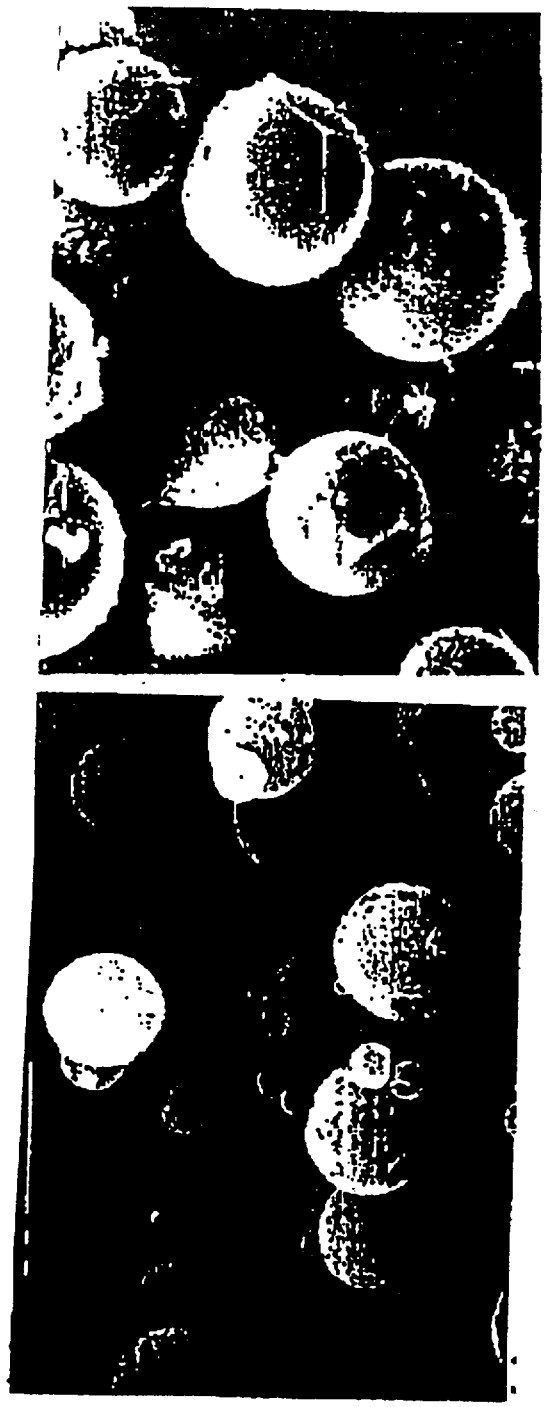

The beads made using acetone as porogenic solvent (FIG. 2d) differed from the others. They were larger, had much rougher surface morphology and more "debris" on their surfaces than those prepared using chloroform or toluene. The beads made with toluene as porogenic solvent had a less dense surface shell and somewhat more porous interior structure than those made with chloroform. FIG. 2b shows beads of polymer PF9 which has a lower proportion of cross-linker than that in FIG. 2a (polymer PF2). The beads in FIG. 2b are much more irregular and distorted, suggesting that these particles might remain softer and deformable for longer during polymerization and hence are more prone to distortion due to shear or collision. The internal morphology of these beads also appeared to be more open and porous than that of polymer PF2. This might contribute to the better HPLC performance of the latter. The beads of FIG. 2(c) show PF13 beads and FIG. 2(e) PF15 beads.

High Pressure Liquid Chromatography

To confirm that the polymer beads made according to the present invention are molecularly imprinted, and that the quality of the recognition sites is at least as good as that obtained by traditional bulk polymerization methods, a range of polymers imprinted using Boc-Phe were evaluated by HPLC. This system was chosen since a great deal of information is available on the performance of traditional crushed bulk polymers imprinted with Boc-Phe.

Beads were suspended in a chloroform-acetone (17:3) mixture by sonication and slurry packed into 10 cm by 0.46 cm or 25 cm by 0.46 cm stainless steel columns at 300 bar using an air driven fluid pump and acetone as solvent. The columns were washed with 250 ml methanol: acetic acid (9:1) and then equilibrated with chloroform containing 0.1% or 0.25% acetic acid. 10 g Boc D- or L- Phe or 20 μg racemate in 20 μl solvent was injected and chromatograms recorded at 254 nm at a flow rate of 0.5 ml/min. Some separations were also run at higher flow rates and with larger amounts of compound loaded. Chromatographic parameters were calculated using standard theory.

The results for HPLC evaluation of six of the polymers are summarized in Table 2.

TABLE 2

| ID† | Ratio‡ | % x-link | K'D | K'L | Alpha | Rs | f/g |
|---|---|---|---|---|---|---|---|
| | | | CHCl$_3$ + 0.1% Acetic Acid | | | | |
| PF2 | 1:4 | 80 | 0.69 | 1.44 | 2.09 | 0.59 | 0.51 |
| PF8 | 1:8 | 71 | 0.77 | 1.42 | 1.88 | 0.43 | 0.37 |
| PF9 | 1:12 | 62.5 | 1.12 | 1.88 | 1.68 | 0.83 | 0.73 |
| PF10 | 1:16 | 56 | 1.44 | 2.81 | 1.81 | 0.49 | 0.5 |
| PF11 | 1:12 | 75 | 0.71 | 1.27 | 1.8 | 0.87 | 0.63 |
| PF11* | 1:12 | 75 | 0.79 | 1.43 | 1.82 | 1.23 | 0.84 |
| PF12 | 1:4 | 80 | 0.7 | 0.7 | 0 | 0 | 0 |
| | | | CHCl$_3$ + 0.25% Acetic Acid | | | | |
| PF2 | 1:4 | 80 | 0.43 | 0.78 | 1.81 | 0.26 | 0.23 |
| PF8 | 1:8 | 71 | 0.54 | 0.97 | 1.79 | 0.31 | 0.28 |
| PF9 | 1:12 | 62.5 | 0.76 | 1 | 1.7 | 0.69 | 0.66 |
| PF10 | 1:16 | 56 | 0.5 | 1.89 | 1.89 | 0.48 | 0.44 |
| PF11 | 1:12 | 75 | 0.63 | 0.71 | 1.78 | 0.48 | 0.39 |
| PF11* | 1:12 | 75 | 0.84 | 1.11 | 1.91 | 1.08 | 0.88 |
| PF12 | 1:4 | 80 | 0 | 0.54 | 0 | 0 | 0 |

†The identification scheme (ID) for the polymers is consistent with the notation developed previously at Table 1.
‡The ratio shown is that of the print molecule to the methacrylic acid (MAA) monomer.

As the ratio of MAA to print molecule increased the retention times and hence the capacity factors increased due to greater non-specific interaction. The α-values, however, stayed almost constant at about 1.8. This is very similar to values obtained under similar conditions for ground and sieved bulk Boc-Phe polymers (range 1.77 to 2.17). The optimum resolution was found at an MAA:Boc-Phe ratio of 12:1, the value of 0.83 being good for a 10 cm column. Using a longer column (25 cm) of polymer PF11 resulted in near baseline resolution of the enantiomers as has previously been reported for bulk polymers (chromatogram not shown). Polymer PF9, which was only 62.5% cross-linked, performed better than polymer PF11, which had the same print molecule:MAA ratio but was 75% cross-linked. It has previously been shown that separations improve as the degree of cross-linking increases within this range, but this was not observed in these experiments. Polymer PF11 was made using less print molecule (see Table 1) since it is not possible too vary these parameters independently, and it is thus not clear whether the improved resolution was due to the larger number of binding sites or to changes in polymer morphology as a result of the lower cross-linking. Such observations indicate that significant improvements in separation can be achieved by careful optimization of the many compositional and operational variables. The simplicity and speed of the bead polymerization method makes extensive optimization possible.

Figure 2E:
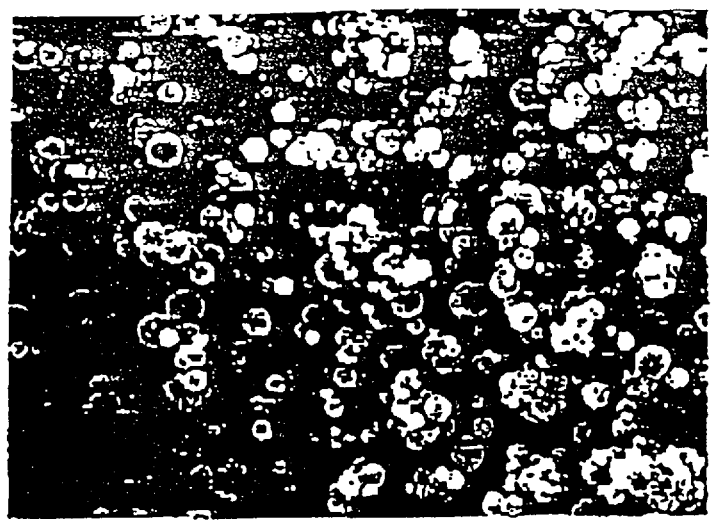

It has previously been suggested that polymers based on the trifunctional cross-linker TRIM had much better resolution and load capacity than EDMA-based polymers for a range of di and tripeptides. In order to further evaluate the suspension polymerization method according to the present invention, imprints of Boc-L-Phe were made in a TRIM-based polymer. Beads produced using 100 mg of PFPS (PF15) had an average diameter of 5.7 cm, and those using 25 mg PFPS (PF16) a diameter of 18.8 μm, very similar to what would have been expected for EDMA-based polymers with the same amount of stabilizing polymer. Thus, in terms of bead-size prediction, TRIM and EDMA seem to behave very similarly. An SEM picture of beads of PF15 is shown in FIG. 2e. These beads were tested by HPLC and gave excellent resolution and high load capacities, as was noted for the ground and sieved block polymers. The packed column had very low back pressure, and high resolution could be achieved, even at quite high flow rates.

FIGS. 3a–3e shows a series of chromatograms for flow rates between 0.5 and 5 mlmin$^{-1}$, i.e., 0.5 ml/min, 1 ml/min, 2 ml/min, 3 ml/min and 5 ml/min. Little difference was observed between 0.5 and 2 mlmin$^{-1}$, suggesting that diffusion rates are rapid for these small beads. The back pressure was very low and resolution excellent (fg=0.89, 0.89 and 0.85 at 0.5, 1 and 2 mlmin-1 respectively). Reasonable resolution (f/g=0.61) was still achieved at 5 mlmin-1 (back pressure 1300 psi). Ground and sieved random <25 μm particles do not usually perform well at flow rates above 1 mlmin-1. Working with crushed bulk polymers in the 5 μm size range is difficult. Extensive defining is required to avoid high back pressures in HPLC columns, and sieves below 10 μm are unobtainable, making it necessary to use alternative size fractionation techniques. This result indicates that the beaded imprinted polymers should have significant advantages over "traditional" ground and sieved block polymers, both in the case of preparation and in the performance of the resulting columns.

It is also contemplated that because the stabilizer of the present invention is essentially chemically inert, it may be used as a dispersant for making beaded polymers containing water-sensitive monomer units, e.g., acid chlorides or anhydrides.

Although the foregoing invention has been described in some detail by way of illustration and example for purposes of clarity of understanding, it will be obvious to those skilled in the art that certain changes and modifications may be practiced without departing from the spirit and scope thereof as described in the specification and as defined in the appended claims.

We claim:

1. A suspension polymerization stabilizer comprising a copolymer containing monomer units A defined as $C_nF_{2n+1}SO_2N(C_2H_5)C_2H_4$—O—CO—CH=CH$_2$ and comonomer units B defined as $CH_3O(CH_2CH_2O)_mC_2H_4$—O—CO—CH=CH$_2$; where n is between 1 and 20 and m is between 10 and 70 and about 500.

2. The stabilizer according to claim 1, wherein n is about 7.5 and m is about 43.

3. A polymer defined by the formula

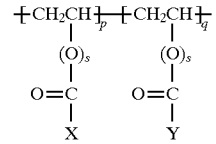

wherein

X is $C_nF_{2n+1}$, $C_nF_{2n+1}(CH_2)_rO$—, $C_nF_{2n+1}O$— or $C_nF_{2n+1}SO_2N(C_2H_5)C_2H_2$—O;

Y is $(Z)_tCH_3O(CH_2CH_2O)_mC_2H_2$—O or $(Z)_tCH_3O(CH_2CH_2O)_m$—

Z is a print molecule;

n is between 1 and 20;

m can be zero to about 500;

p is at least 1;

q can be zero or any positive number;

r is 1–20, preferably 1 or 2;

s is zero or 1; and t is zero or 1.

4. A polymer defined by the formula

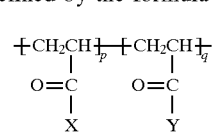

wherein

X is $C_nF_{2n+1}SO_2N(C_2H_5)C_2H_2$—O;

Y is $CH_3O(CH_2CH_2O)_mC_2H_2$—O;

n is between 1 and 20;

m is between 0 and 500;

p is at least 1; and q zero or any positive integer.

5. The stabilizer according to claim 1, wherein n is about 7.5 and m is about 43.

6. A stable emulsion comprising an emulsion of imprinting molecules in liquid perfluorocarbons containing polyoxyethylene ester groups.

7. The emulsion according to claim 6, wherein said liquid fluorocarbon is a copolymer.

8. The emulsion according to claim 7, wherein said copolymer is formed from the polymerization of monomer A and comonomer B, wherein monomer A is defined as $C_2F_{2n+1}SO_2N(C_2H_5)C_2H_4$—O—CO—CH=CH$_2$, and comonomer B is defined as $CH_3O(CH_2CH_2O)_mC_2H_4$—O—CO—CH=CH$_2$, where n is between 1 and 20, and m zero to about 500.

9. An emulsion comprising imprinting molecules and a polymer defined by the formula

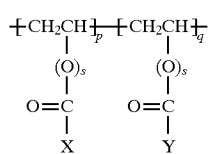

wherein

X is $C_nF_{2n+1}$, $C_nF_{2n+1}(CH_2)_rO—$, $C_nF_{2n+1}O—$ or $C_nF_{2n+1}SO_2N(C_2H_5)C_2H_4—O$;

Y is $(Z)_tCH_3O(CH_2CH_2O)_mC_2H_4—O$ or $(Z)_tCH_3O(CH_2CH_2O)_m—$

Z is a print molecule;

n is between 1 and 20;

m can be zero to about 500;

p is at least 1;

q can be zero or any positive number;

r is 1–20, preferably 1 or 2;

s is zero or 1; and t is zero or 1.

10. An emulsion comprising imprinting molecules and a polymer defined by the formula

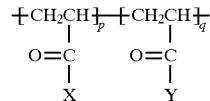

wherein

X is $C_nF_{2n+1}SO_2N(C_2H_5)C_2H_4—O$;

Y is $CH_3O(CH_2CH_2O)_mC_2H_4—O$;

n is between 1 and 20;

m is zero to about 500;

p is at least 1; and q is zero or any positive integer.

* * * * *